United States Patent [19]

Hill

[11] 4,030,481

[45] June 21, 1977

[54] MANOMETRIC PRESSURE SENSING AND LIQUID EVACUATING DEVICE FOR INTRAOPERATIVE HIATAL HERNIA REPAIR

[76] Inventor: Lucius D. Hill, 522 McGilvra Blvd. E., Seattle, Wash. 98102

[22] Filed: Oct. 29, 1975

[21] Appl. No.: 626,759

[52] U.S. Cl. .............................. 128/2 S; 128/350 R
[51] Int. Cl.² ........................ A61B 5/10; A61M 25/00
[58] Field of Search ... 128/2 R, 128/2 S, 348, 349 R, 350 R, 276

[56] References Cited

UNITED STATES PATENTS

| | | | |
|---|---|---|---|
| 3,114,373 | 12/1963 | Andersen | 128/350 R |
| 3,437,088 | 4/1969 | Bielinski | 128/2 S |
| 3,480,003 | 11/1969 | Crites | 128/2 S |

FOREIGN PATENTS OR APPLICATIONS

| | | | |
|---|---|---|---|
| 790,091 | 9/1935 | France | 128/2 S |

Primary Examiner—Dalton L. Truluck
Attorney, Agent, or Firm—Seed, Berry, Vernon & Baynham

[57] ABSTRACT

A device for making intraoperative pressure studies after repair but while the stomach is being evacuated. The device includes a nasal gastric suction tube having a perforated end region with a closed tip and having secured thereto a pressure-sensing tube with a closed end and which is provided with a pressure-sensing opening a known distance up from the closed tip of the nasal gastric tube.

5 Claims, 2 Drawing Figures

MANOMETRIC PRESSURE SENSING AND LIQUID EVACUATING DEVICE FOR INTRAOPERATIVE HIATAL HERNIA REPAIR

BACKGROUND OF THE INVENTION

Field of the Invention

This invention pertains to medical instruments, and more particularly, to a pressure-sensing device suitable for use during hiatal hernia repair.

Hiatal hernia repair is needed in a large number of patients suffering from esophagitis. A hiatal hernia is defined as an enlarged opening at the point where the esophagus goes through the diaphragm. A relatively small hernia will permit the lowest part of the esophagus to slide upward into the chest while a larger hernia will let part of the stomach slide upward. In both cases the sphincter muscle has stretched and lost its capability of holding the stomach's acidic contents from refluxing or flowing back up into the esophagus.

A present repair technique for hiatal hernia is described in Hospital Practice, April 1972, Volume 7, No. 4 at pages 116-124 and in Time Magazine, Mar. 28, 1969 as well as in additional other articles in medical journals. The present preferred procedure is to stitch a part of the stomach to form an internal flap that prevents reflux. Ligaments and other tissues are attached where the esophagus joins the stomach (gastroesophageal junction) so that the junction is anchored permanently below the diaphragm. In addition, the sphincter muscle is tightened around the junction to prevent refluxing of the acidic contents of the stomach.

One of the difficulties in performing hiatal hernia repair is in determining whether the sphincter muscle has been tightened sufficiently to avoid reflux. To determine this in the past, postoperative pressure tests have been employed using various types of pressure-sensing tubes. Examples of such tubes are (1) a tube having a side-opening pressure-sensing hole which is encased in a flexible liquid filled balloon, (2) a tube containing axially spaced electrical strain gauges for simultaneously measuring esophageal, spincter, and gastric pressures, (3) a series of three tubes each with an independent pressure-sensing side hole, each side hole being spaced a different axial distance from the distal end of the collective tubes. None of these pressue-sensing device has proven satisfactory for intraoperative pressure sensing study. Thus, in the absence of a successful intraoperative pressure-sensing device, an inadequate sphincter repair was not detected until after the patient was removed from the surgery room sometimes requiring a second repair operation.

SUMMARY OF THE INVENTION

It is an object of this invention to provide an intraoperative pressure-sensing device for hiatal hernia repair.

It is another object of this invention to provide a device for simultaneously evacuating liquids from the stomach while measuring pressure.

It is still a more specific object of this invention to provide a device for simultaneously evacuating the liquid contents of the stomach while making intraoperative, postrepair pressure-sensing measurements of the sphincter at the gastroesophageal junction.

Basically these objects are obtained by combining a nasal gastric vacuum tube having a closed tip with liquid receiving openings at the lower end adjacent the tip and having connected therewith a flexible, soft, pressure-sensing tube having a pressure-sensing opening located at a known distance from the tip of the nasal gastric suction tube. In the preferred embodiment, the pressure-sensing opening is in the sidewall of the pressure-sensing tube with the pressure-sensing tube having a closed end terminating within the nasal gastric tube for ease of insertion and removal of the device. It is also apparent, of course, that the pressure-sensing tube can terminate in a pressure-sensing opening in the end of the pressure-sensing tube which is located at some known distance up from the tip of the nasal gastric suction tube. Preferably the known distance of the pressure-sensing opening from the tip of the nasal gastric suction tube is about 8 centimeters so that a surgeon can calculate the location of the pressure-sensing opening in the gastroesophageal region by observing the location of the tip of the nasal gastric suction tube relative to the esophageal gastric junction. Preferably also the perssure-sensing tube will be continuously irrigated to keep the pressure-sensing opening free of mucus buildup or other clogging materials.

With the use of this pressure-sensing and stomach evacuating tube, the surgeon is able to make pressure studies while the incision remains open but after the repair has been completed. These studies will enable the surgeon to know instantaneously if the sphincter muscle has been secured tightly enough to provide a long-lasting sphincter repair. The preferred range of sphincter pressures desired at the intraoperative post-repair is between 40 and 50 millimeters of mercury, although a range between 35 to 55 millimeters may prove acceptable under some conditions. This will yield a postoperative pressure between 22 to 25 millimeters of mercury at a normal stomach pressure. The normal sphincter pressure for a healthy gastroesophageal junction is about 15 millimeters of mercury. The higher postoperative pressure is desired and provides sufficient excess in sphincter pressure to allow for continued deterioration with patients which have experienced a tendency for such deterioration. Thus, the sphincter pressure can remain at or above normal for many years and possibly for the life of the patient.

DETAILED DESCRIPTION OF THE FIGURES OF THE DRAWING

Figure 1:
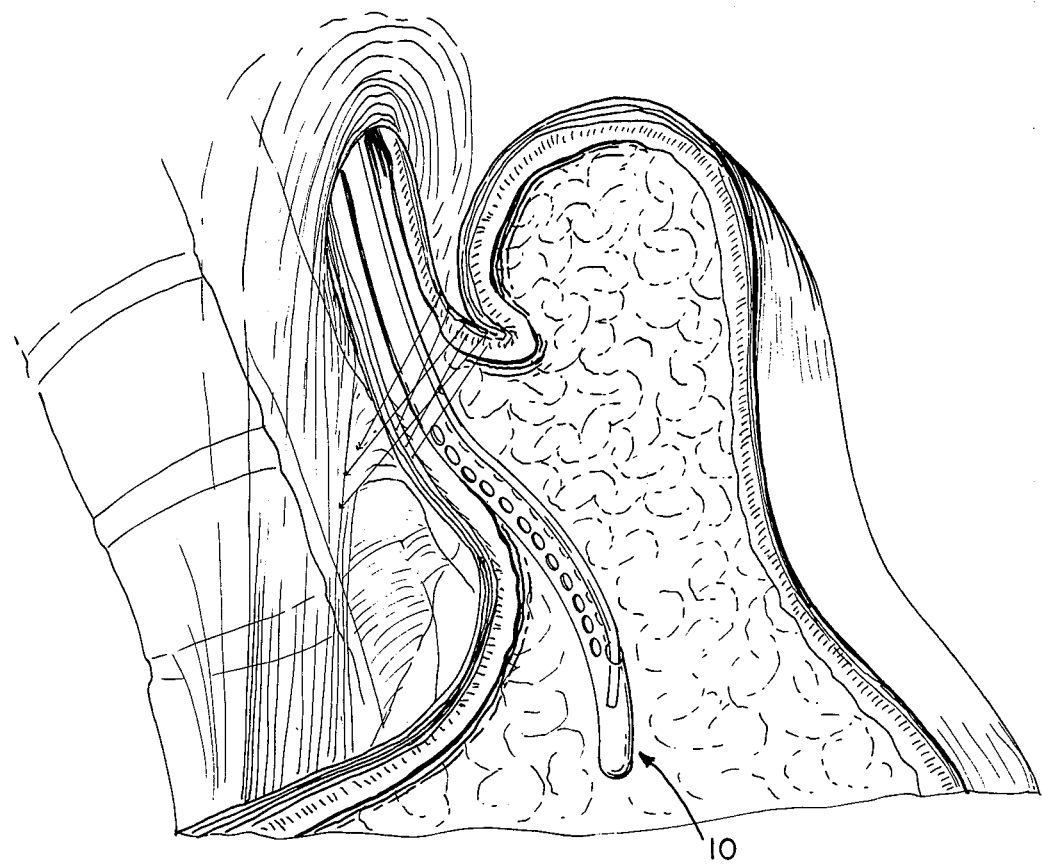
FIG. 1 is a perspective illustration of the combined pressure-sensing and liquid-evacuating device shown illustrated in place after a repaired hiatal hernia.
Figure 2:
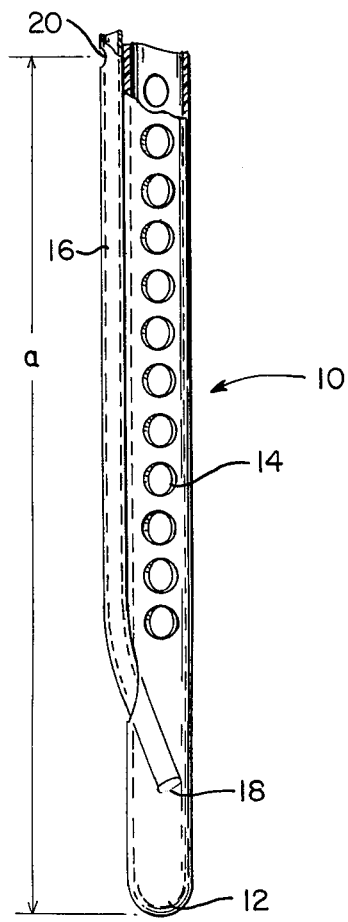
FIG. 2 is an enlarged isometric of the combined tubes.

The combined pressure-sensing and liquid-evacuating device 10 includes a conventional nasal gastric suction tube which is provided with a closed tip 12 and a plurality of liquid receiving openings 14. The upper end of the tube is connected to a conventional Gonco suction pump which evacuates the stomatc and intermittently empties the contents externally of the stomach. The evacuation leaves the stomach in a deflated condition, approximately 20 to 25 millimeters of mercury below its normal pressure.

Secured to the wall of the nasal gastric suction tube is a smaller diameter pressure-sensing tube 16 having a closed end 18 and a pressure-sensing side opening 20. Preferably the pressure-sensing tube terminates within the nasal gastric suction tube for ease of insertion and removal of the combined tubes. Preferably the pressure-sensing tube is of a highly flexible soft material, such as silastic. Suitable combined tubes which can be modified to form this invention for pressure studies are called Anderson tubes manufactured by Anderson Products, Oyster Bay, N.Y.

The standard Anderson tube comes with an open tip within the larger tube. Thus, the conversion requires sealing or closing the tip of the smaller tube and providing a pressure-sensing hole in the side wall of the smaller tube. Preferably the side opening 20 is located 8 centimeters (but other known distances will suffice) from the tip of the larger tube so that the surgeon can determine the location of the side opening 20 merely by observing, either by eye or by touch, the location of the tip within the stomach and esophageal region.

In a preferred operation the nasal gastric suction tube is connected to a Gonco suction pipe while the pressure-sensing tube is connected through a pressure transducer to a strip chart recording. A perfusion pump is also connected to the pressure-sensing tube to perfuse liquid downwardly through the pressure-sensing tube to maintain the opening 20 in a continuously flushed condition. With alternative ways of keeping the opening 20 open, a nonflowing column of water may also be satisfactory to transfer the pressure reading to the transducer. A suitable transducer is a Statham Transducer Model P23Dc. Similarly a Harvard profusion pump with a 150 cc Luer Lok syringe provides the irrigating liquid.

The preferred technique is to make a preoperative reading prior to anesthetizing the patient, next make prerepair but intraoperative readings of the anesthetized patient, then intraoperative postrepair readings and finally a postoperative reading when the patient is again removed from surgery. The important reading is the postrepair intraoperative reading which tells the surgeon whether the sphincter repair has been successful and allows for additional stitching or adjustments of the stitching to tighten the sphincter if the pressure readings are found to be too low. The additional prerepair readings are particularly helpful in learning desired anticipated pressure values for various patients but once the operation has been performed often enough the intraoperative postrepair pressure study will produce sufficient data along to predict whether the repair is successful.

While the preferred embodiments of the invention have been illustrated and described, it should be understood that variations of this device will be apparent to one skilled in the are without departing from the principles expressed here. Accordingly, the invention is not to be limited to the specific embodiment illustrated in the drawing.

The embodiments of the invention in which a particular property of privilege is claimed are defined as follows:

1. A pressure-sensing and liquid-evacuating device for measuring sphincter pressure during intraoperative hiatal hernia repair operations, comprising:
    a nasal gastric suction tube for emptying liquids from the stomach and having a tip, a plurality of openings adjacent the tip for allowing passage of liquids into the tube, and an open upper end adapted to be connected to a vacuum source, and
    a smaller, soft, flexible pressure-sensing tube secured to said nasal gastric suction tube and having an uncovered, pressure-sensing single opening located externally of the nasal gastric suction tube and a short distance from the tip of said nasal gastric suction tube, with the pressure sensing opening adapted to be exposed directly to the interior of the stomach or esophagus, and engagable by the sphincter muscle whereby the pressure of the stomach, sphincter muscle and esophagus can be sensed immediately following the repair while simultaneously removing liquid from the stomach.

2. The device of claim 1, said pressure-sensing tube being closed below said single opening and said pressure-sensing tube having an end spaced from the single opening and terminating within the nasal gastric suction tube.

3. A pressure-sensing and liquid-evacuating device for measuring sphincter pressure during intraoperative hiatal hernia repair operations, comprising:
    a nasal gastric suction tube for emptying liquids from the stomach and having a tip, a plurality of openings adjacent the tip for allowing passage of liquids into the tube, and an open upper end adapted to be connected to a vacumm source, and
    a smaller, soft, flexible pressure-sensing tube secured to said nasal gastric suction tube and having a pessure-sensing opening located a short distance from the tip of said nasal gastric suction tube whereby the pressure of the stomach, sphincter muscle and esophagus can be sensed immediately following the repair while simultaneously removing liquid from the stomach,
    said pressure-sensing opening being located a known distance up from the tip of the suction tube so that the location of the pressure-sensing opening in the gastroesophageal junction can be accurately determined by sensing the location of the tip of the nasal gastric suction tube.

4. A method of using a pressure-sensing tube for intraoperative hiatal hernia repair, comprising
    inserting into the patient's stomach a pressure-sensing tube with a pressure-sensing opening a short known distance up from the closed tip of a nasal gastric suction tube, continuously removing liquids from the stomach and as a result bringing the internal stomach pressure to a reduced pressure of about 20 millimeters of mercury, irrigating the pressure-sensing opening to keep it open and clean,
    repairing the hiatal hernia, and
    while the incision is still opened, slowly withdrawing the pressure-sensing tube while observing the pressure reading until the pressure-sensing opening is located at the sphincter muscle and specifically observing a lower esophageal sphincter pressure of 35–55 millimeters of mercury to assure a postoperative sphincter pressure of about 22–25 millimeters of mercury at a normal internal stomach pressure assuring a sufficiently tight repair.

5. The method of claim 4, wherein the pressure-sensing tube is secured to a nasal gastric suction tube for combining the continuous liquid removal with the pressure sensing.

* * * * *